United States Patent
Quate et al.

(10) Patent No.: US 6,436,647 B1
(45) Date of Patent: Aug. 20, 2002

(54) METHOD FOR DETECTING CHEMICAL INTERACTIONS BETWEEN NATURALLY OCCURRING BIOLOGICAL ANALYTE MOLECULES THAT ARE NON-IDENTICAL BINDING PARTNERS

(75) Inventors: Calvin F. Quate, Stanford; Mark O. Trulson, San Jose; Scott R. Manales, Santa Barbara; Jonathan E. Forman, San Jose, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/812,706

(22) Filed: Mar. 19, 2001

Related U.S. Application Data

(63) Continuation of application No. 09/097,675, filed on Jun. 16, 1998, now Pat. No. 6,203,983.
(60) Provisional application No. 60/049,707, filed on Jun. 16, 1997.

(51) Int. Cl.[7] .................. C12Q 1/68; G01N 33/553
(52) U.S. Cl. .......................... 435/6; 435/526
(58) Field of Search ............... 435/6; 436/526

(56) References Cited

U.S. PATENT DOCUMENTS

| | | |
|---|---|---|
| 5,372,930 A | 12/1994 | Colton et al. |
| 5,510,481 A | 4/1996 | Bednarski et al. |
| 5,807,758 A | 9/1998 | Lee et al. |

OTHER PUBLICATIONS

"Nanometers, Picowatts, Femtojoules: Thermal Analysis and Optical Spectroscopy Using Micromechanics," Rudiger Berger et al., *Analytical Methods & Instrumentation, Special Issue μTAS '96*, 4 pages.

"Observation of a chemical reaction using a micromechanical sensor," J.K. Gimzewski et al., *Chemical Physics Letters*, Jan. 28, 1994, vol. 217, No. 5.6, 7 pages.

"Automated parallel high–speed atomic force microscopy," S.C. Minne et al., *American Institute of Physics*, May 4, 1998, 3 pages.

"Interdigital cantilevers for atomic force microscopy," S.R. Manalis et al., *American Institute of Physics*, Dec. 16, 1996, 3 pages.

"Two dimensional micromechanical bimorph arrays for detection of thermal radiation," S.R. Manalis et al., *Applied Physics Letters*, 3 pages.

"Surface Stress in the Self–Assembly of Alkanethiols on Gold," R. Berger et al., submitted to *Science*—Feb. 27, 1997, 8 pages.

"Sequential position readout from arrays of micromechanical cantilever sensors," H.P. Lang et al., *American Institute of Physics*, accepted for publication Nov. 12, 1997, 3 pages.

*Primary Examiner*—Eggerton A. Campbell
(74) *Attorney, Agent, or Firm*—Banner & Witcoff, Ltd.

(57) ABSTRACT

A method of using micromechanical devices as sensors for detecting chemical interactions between naturally occurring bio-polymers which are non-identical binding partners is provided. The method is useful whether the reactions occur through electrostatic forces or other forces. Induced stress, heat, or change in mass is detected where a binding partner is placed on a cantilever for possible reaction with an analyte molecules (i.e., a non-identical binding partner). The method is particularly useful in determining DNA hybridization but may be useful in detecting interaction in any chemical assay.

24 Claims, 2 Drawing Sheets

Figure 1:
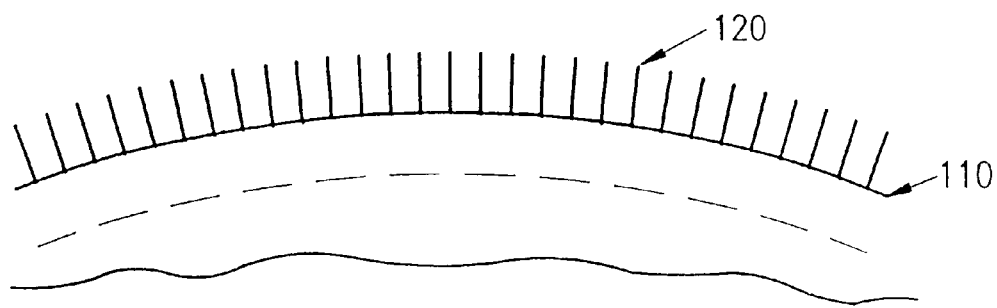

METHOD FOR DETECTING CHEMICAL INTERACTIONS BETWEEN NATURALLY OCCURRING BIOLOGICAL ANALYTE MOLECULES THAT ARE NON-IDENTICAL BINDING PARTNERS

The present application is a continuation of U.S. application Ser. No. 09/097,675 filed Jun. 16, 1998 now U.S. Pat. No. 6,203,983 claim priority to U.S. Provisional No. 60/049,707 filed Jun. 16, 1997, which is hereby incorporated by reference for all it discloses and for all purposes.

FIELD OF THE INVENTION

The present invention relates to the field of micromechanical devices as sensors for detecting physical or chemical changes caused by chemical interactions between naturally occurring bio-polymers which are non-identical binding partners, such as can occur with polyamino acids, polynucleotides, and the like. The method of the present invention is useful whether the reactions occur through electrostatic forces or through other forces. In particular, the present invention provides a method for detecting chemical interactions between naturally occurring bio-polymers which are non-identical binding partners where one binding partner or probe molecule is placed on a cantilever for possible reaction with a sample analyte molecule (i.e., a non-identical binding partner). The physical or chemical change may be induced stress, heat, or mass, for example. The present invention is particularly useful in determining DNA hybridization but may be used in detecting interactions between any analyte molecules, whether monomeric or polymeric. Examples of polymer arrays which can be used with the method of the present invention include nucleic acid arrays, protein or polypeptide arrays, carbohydrate arrays, and the like.

BACKGROUND OF THE INVENTION

As known in the art, various techniques have been used to determine whether a chemical interaction has occurred between two materials, such as between a probe carrying a binding partner and a sample. In the specific example of determining whether DNA hybridization has occurred, various techniques have been used to extract information from a sample. For example, detection schemes have been used that are responsive to fluorescence in order to reveal specific interactions or hybridizations. U.S. Pat. No. 5,578,832, "Method and Apparatus for Imaging a Sample on a Device," issued to Trulson et al. ("the '832 patent") and U.S. Pat. No. 5,631,734, "Method and Apparatus for Detection of Fluorescently Labeled Materials," issued to Stern et al. ("the '734 patent") provide methods and systems for detecting a labeled marker on a sample located on a support through the use of an excitation radiation source and radiation optics. The '832 patent and the '734 patent are hereby incorporated by reference for all they disclose and for all purposes. As described in the '832 and '734 patents, these techniques employ the use of a label, for example, the DNA probe is labeled with a fluorescent molecule, such as fluorophore or biotin. Once the DNA probe is labeled according to prior methods, an optical system can be used to determine whether hybridization has occurred by measuring fluorescence activated between the labeled sample and the probe material.

The present invention provides a method for determining whether a chemical interaction has occurred between naturally occurring bio-polymers which are non-identical binding partners through detecting a physical or chemical change on a micromechanical device called a cantilever. A cantilever, by way of analogy, can be thought of as a diving board which has been reduced to a very small size. More specifically, a cantilever is a physical device that is attached to another object at one end and remains free to move on the other end. Deflection or up and down movement of the free end of the cantilever can then be detected. The method of the present invention can be used with any chemical analyte to generate a physical or chemical change, whether through affinity binding, which may include hydrogen bonding, electrostatic attractions, hydrophobic effects, dipole interactions, or through other forces.

The use of micromechanical sensors is advantageous in the method of the present invention for several reasons. Various signals such as force, heat, stress, magnetism, charge, radiation and chemical reactions can be readily transduced into a micromechanical deflection by an appropriately coated structure, such as a cantilever. In addition, silicon-based micromechanical devices can easily be integrated into microelectronic processing systems such as CMOS (Complementary Metal-Oxide-Semiconductor), as known to one of skill in the art. As a result, it is possible to produce seamless sensors as low cost and to integrate them directly into computers. Moreover, micromechanical sensors are very small, typically approximately 400 $\mu$m in length, approximately 40 $\mu$m wide and approximately 1 $\mu$m thick. As a result, it is possible to obtain a short response time, generally measured in microseconds, as well as sensitivity superior to standard techniques. Finally, it is possible to construct arrays of micromechanical devices, thereby permitting complex analysis of a variety of signals as well as the use of a variety of sensing materials.

By way of background, it is known that stress induced by self-assembled monolayers can be detected by observing the deflection of a micromachined cantilever similar to those used in the commercial Atomic Force Microscope ("AFM"), as described by Berger et al., in "Surface Stress in the Self-Assembly of Alkanethiols on Gold," Science, Jun. 27, 1997, Vol. 176, p. 2021 ("Berger I"), which is hereby incorporated by reference for all it teaches. The Berger et al. paper studied the surface stress changes during self-assembly of selected molecules, including alkanethiol molecules self-assembled on gold. The researchers found that the stress increases linearly with the length of the alkyl chain of the molecule. In addition, the researchers detected a change in the state of stress with the formation of salt bridges formed when mercaptohexadecanoic acid was deposited on a functionalized surface coated with the self-assembled thiols. This change in cantilever stress was used to detect the formation of the salt bridges when the analyte molecules were introduced.

Other pertinent work involving michromechanical sensors is reflected in a paper by Berger et al. entitled "Nanometers, Picowatts, Femtojoules: Thermal Analysis and Optical Spectroscopy Using Micromechanics," Analytical Methods & Instrumentation, Special Issue, $\mu$TAS '96 ("Berger II"), also incorporated by reference for all it discloses and for all purposes. In Berger II, examples of low-cost, disposable micromechanical devices are described which perform optical absorption spectra, calorimetric and thermal analysis, electrochemical stressograms, gas phase adsorption and surface reaction monitors.

Other work in the area of micromechanical sensors is reported by Gimzewski et al. in "Observation of a chemical reaction using a micromechanical sensor," Chemical Physics Letters, Vol. 217, No. 5,6, Jan. 28, 1994, ("Gimzewski")

which is hereby incorporated by reference for all it discloses and for all purposes. Gimzewski discloses a calorimeter for sensing chemical reactions. The device is based on a micromechanical silicon lever coated with a layer of aluminum. A sample is deposited on the lever in a thin layer. Heat fluxes are detected by measuring the deflection of the cantilever induced by the differential thermal expansion of the lever. Specifically, Gimzewski discloses using this technique to review the catalytic conversion of $H_2+O_2$ to obtain $H_2O$.

It is further known to operate multiple probes for the atomic force microscope. As described by Minne et al., "Automated parallel high-speed atomic force microscopy," Applied Physics Letters, Volume 78, No. 18, May 4, 1998 ("Minne"), which is herein incorporated by reference for all it discloses and for all purposes, an expandable system is provided to operate multiple probes for the atomic force microscope in parallel at high speeds. The cantilever footprint is only 200 µm wide which allows the devices to be placed in a one-dimensional expandable parallel array.

Yet another contribution to the art of micromechanical sensors is described by Manalis et al., "Interdigital cantilevers for atomic force microscopy," Applied Physics Letters, Vol. 69, No. 25, Dec. 16, 1996 ("Manalis I"), which is hereby incorporated by reference for all it discloses and for all purposes. In Manalis I, an AFM sensor is described in which a silicon cantilever is micromachined into the shape of interdigitated fingers that form a diffraction grating. When detecting a force, alternating fingers are displaced while remaining fingers are held fixed. As a result, a phase sensitive diffraction grating is created which allows the cantilever displacement to be determined by measuring the intensity of diffracted modes.

Another paper by Lang et al., "Sequential position readout from arrays of micromechanical cantilever sensors," Applied Physics Letters, Vol. 73, p. 383, 1998 ("Lang") describes using a reference cantilever for canceling environmental noise. Lang is hereby incorporated by reference for all it discloses and for all purposes. In Lang, chemically specific responses are extracted in a noisy environment using a sensor to detect specific chemical interactions and an uncoated cantilever as a reference.

Finally, another paper by Manalis et al., "Two dimensional micromechanical bimorph arrays for detection of thermal radiation," Applied Physics Letters, Jun. 16, 1997, (Manalis II) hereby incorporated by reference for all it discloses and for all purposes, describes fabricating arrays of cantilevers and using them as sensitive detectors of head induced stress. Specifically, the cantilevers described by Manalis II were placed on a grid with 50 microns on centers. The present inventors have determined that this type of array is a suitable substrate for determining, for example, hybridization.

SUMMARY OF THE INVENTION

Rather than using traditional labeling, such as optical or electrochemical labeling, in order to detect chemical interactions between naturally occurring bio-polymers which are non-identical binding partners, the present inventors have determined a new and useful method for "reading" a substrate to determine whether a particular chemical interaction has occurred. In traditional labeling, sample analyte molecules are modified in some way to permit their detection when they combine with the probe molecules. The method of the present invention is particularly useful in the detection of hybridized sites on a DNA probe array. The method of the present invention allows detection of hybridization without modifying either the analyte or the probe molecules, i.e., it requires no labeling.

According to the method of the present invention, a chemical interaction between naturally occurring bio-polymers which are non-identical binding partners is monitored by detecting a physical or chemical change through deflection of a cantilever. The physical or chemical change can be, for example, induced stress on the cantilever which causes the cantilever to move or deflect. Standard AFM techniques are then used to detect the deflection of the cantilever. The physical or chemical change can also be in the form of a heat reaction, which similarly causes the cantilever to deflect or bend where the cantilever is made of two materials, i.e., is a bimorph. A physical or chemical change might also result in a change in mass on the cantilever. In such an example, the resonant frequency of the cantilever will change due to the mass change. Measuring the resonant frequency of the cantilever under such circumstances will allow the physical or chemical change to be detected.

In a specific embodiment of the present invention, oligonucleotides are deposited onto a cantilever. The stress induced by hybridization is detected with methods commonly used for detecting cantilever deflection in the AFM. As is well known to one skilled in the art, these methods are sensitive to the point where deflections less than 0.01 nm can be easily detected. The substrate used according to the method of the present invention allows exploitation of the cantilever's properties in order to detect the hybridized sites.

Specifically, the stress in the individual cantilevers is monitored in the manner shown by Manalis II, noted above. First, the surfaces of the cantilevers are prepared in the same manner now common in immobilized sensor technology, as known to one skilled in the art. Next, a binding partner, such as oligonucleotides, is deposited on the cantilevers to form an array of probes. This deposit will change the state of stress on the individual cantilevers and this stress pattern is used as the reference. When sample or analyte molecules (i.e., a non-identical binding partner) are introduced to the cantilever and interact with the binding partner (probe molecules) at appropriate sites, the stress on the cantilever at the particular site will change as a result of the interaction. The change in stress with the introduction of the sample molecules will be monitored with standard AFM techniques.

The present invention does not use optical or electromechanical labels, as previously described. In addition, it serves as a tool for understanding the processes involved in chemical interactions between naturally occurring bio-polymers which are non-identical binding partners, such as DNA hybridization, by providing additional ways to measure events such as the length of the chemical interaction and the number of molecules hybridized. Moreover, it provides an additional, highly sensitive, low-cost means to monitor chemical interactions, as described in detail below.

DETAILED DESCRIPTION OF THE INVENTION

According to the present invention, a physical or chemical change on a cantilever is measured in order to monitor the occurrence of a chemical interaction between naturally occurring bio-polymers which are non-identical binding partners, for example, between biological polymers or other analytes, monomeric or polymeric. Typically, the cantilever as used with the method of the present invention is approximately 100 µm in length, 50 µm in width and approximately 1 µm in thickness. When a chemical interaction occurs on the cantilever, a physical or chemical change occurs causing the cantilever to be deflected, i.e., moved up or down at its free end. Such deflection motion can be detected to a very fine degree, for example, up to a fraction of a diameter of an atom.

Turning to the specific example of using the present method to detect DNA hybridization, as shown in FIG. 1, the surface of a cantilever 110 is first prepared in order to be able to attach single strands of DNA. Such surface preparations are known to those of skill in the art of DNA hybridization detection methods. More specifically, cantilevers made of a solid substrate, for example silicon or similar materials, are prepared with special surfaces of silicon dioxide ($SiO_2$) and standard procedures are used for making a functionalized layer that allows attachment of probe molecules. Next, a binding partner or probes molecules, for example, single stranded DNA 120, are introduced onto one surface of the cantilever.

Figure 2:
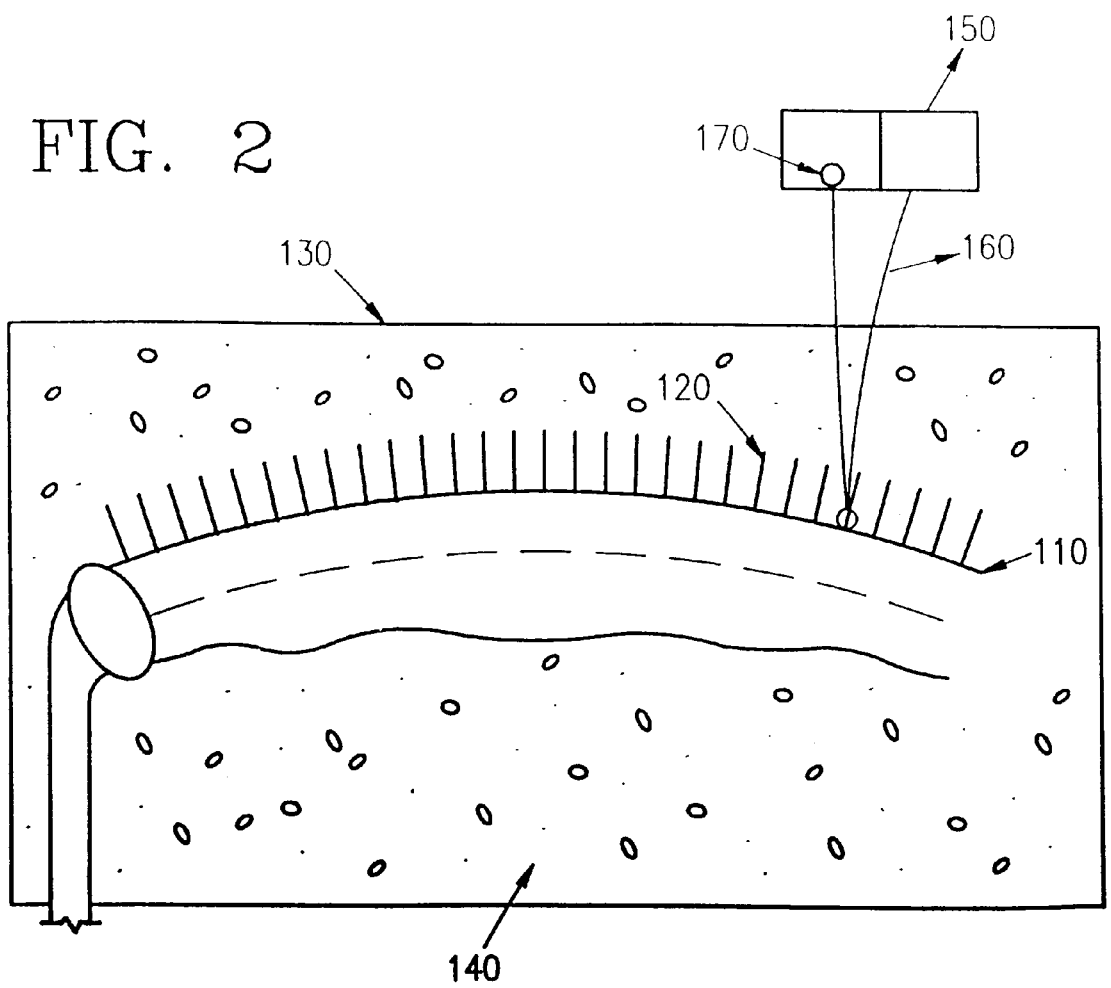

As shown in FIG. 2, the device is then preferably mounted into a liquid cell 130, for example, containing an aqueous buffer 140. A detector 150 is employed in which a laser beam 160 is shown on the cantilever and reflects off of the cantilever. The reflected spot 170 of light is used to determine the relative position of the cantilever. In other words, movement of the cantilever can be determined by directly detecting the movement or angle of the reflected laser beam light. This provides a particular advantage in the present method in that it is always possible to obtain a strong signal from the reflected light.

Figure 3:
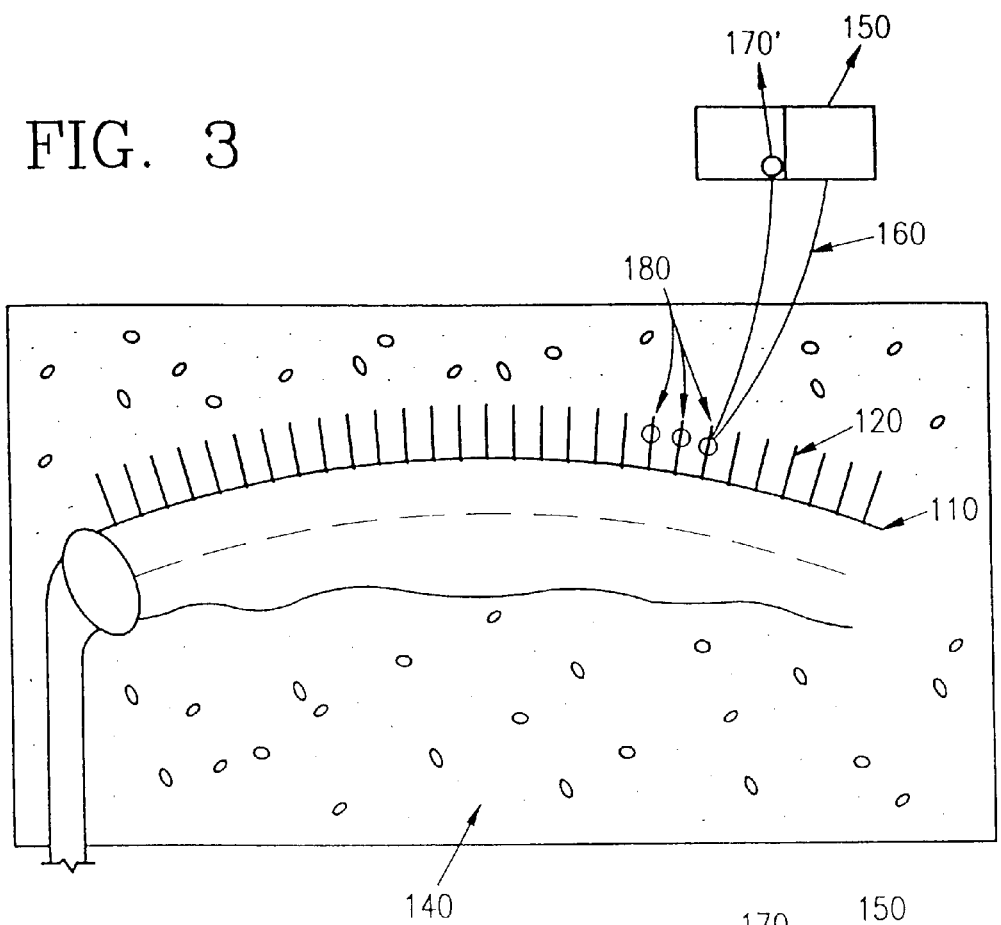

The response from this first deflection on the detector is used as a reference to determine cantilever deflection, as further described. Next, sample analyte molecules, such as DNA is introduced to the surface of the cantilever containing single stranded DNA. The sample analyte molecules will hybridize with selected strands of DNA on the cantilever, as reflected at numeral 180 in FIG. 3. As a result, stress is induced on the cantilever which will cause the cantilever to deflect. More specifically, when hybridization occurs, surface pressure results by the addition of negative charges on the surface of the cantilever because DNA is a polyanion. In other words, hybridization causes more electrostatic charges to build up on the cantilever surface which tend to repel one another. Because the sample analyte molecules are only on one surface of the cantilever, the surface of the cantilever deflects due to this repelling action. This deflection will appear on the deflector as a signal 170' in FIG. 3 which can be correlated against the reference signal. It should be noted that the method of the present invention can be used with negatively charged analytes (such as DNA) or positively charged analytes. In addition, the method of the present invention can also be used with uncharged analytes because forces other than electrostatic forces, such as dipole forces, can be employed with the present method.

The detector used with the present invention can be any optical detector capable of tracking reflected laser light as known to one of ordinary skill in the art, for example, can be a split photodiode, linear array of photodetectors, piezo resistance elements or the like.

Figure 4:
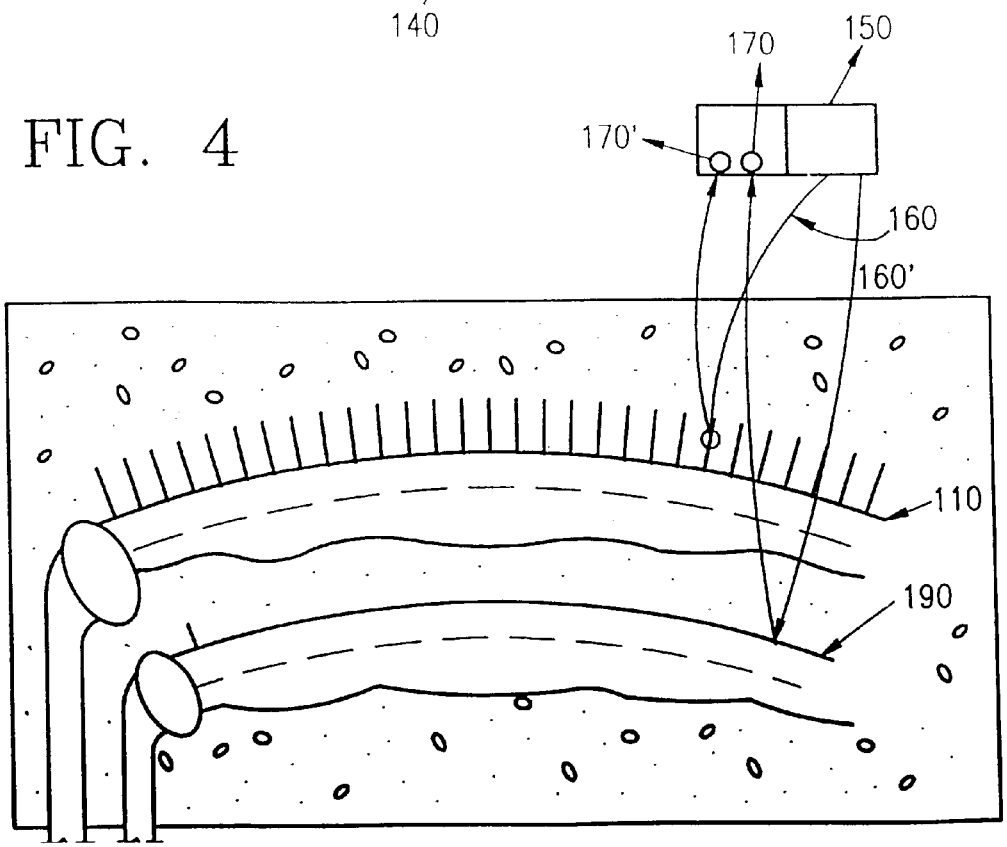

In an alternative embodiment, shown in FIG. 4, a second cantilever 190 can be used as a reference cantilever. The second cantilever 190 is preferably mounted side by side with cantilever 110. In such an embodiment, a surface of the second cantilever 190 is prepared in the same manner as the first cantilever 110 which will be used for hybridization. However, the second cantilever 190 does not have a binding partner, such as single stranded DNA, attached onto one of its surfaces and is not treated with sample analyte molecules, such as DNA. In this case, one signal (numerals 170 and 170' in FIG. 4) from each cantilever is detected by the detector and the difference between the reflected light between the two cantilevers is analyzed. The embodiment shown in FIG. 4 cancels any spurious motion of the cantilever caused, for example, by the environment, such as the liquid in the container.

In either embodiment, the signals detected by the detector are then analyzed in order to determine whether hybridization, for example, has occurred. If there is a change in position after the sample analyte molecules, such as DNA, have been introduced on the single cantilever (single cantilever embodiment), or if the cantilever carrying the sample analyte molecules, such as DNA, has changed its position in relation to the reference cantilever (two cantilever embodiment), hybridization has been detected.

In yet another embodiment, several pairs of cantilevers could be used, with one cantilever carrying a specific probe molecules and the other cantilever of the pair carrying a non-specific probe molecule or no probe molecule at all. In the context of DNA hybridization, for example, several pairs of cantilevers could be used each carrying a different sequence of single stranded DNA. Multiple pairs of cantilevers organized in such a fashion are known as an array of cantilevers. In an array, each cantilever pair includes one cantilever for hybridization and one neutral or reference cantilever. The difference between signals of each cantilever pair in the array provides the true hybridization signal for that pair, similar to the system described with respect to FIG. 4.

With a cantilever array, it is possible to introduce a complex mixture of molecules into the liquid flow cell encompassing the array and to identify those molecules in the complex by determining which cantilevers hybridize. The number of cantilever pairs which can be used in an array is united. Such a cantilever array has practical utility in both biomedical and environmental applications. An example of an environmental application would be to use such a detector to identify an unknown contaminant in a sample of air or water which might have been infected by environmental terrorists. The possible applications for the method of the present invention are limitless.

In still another alternative embodiment, an interdigital array of cantilevers, as described above by Manalis I, can be used in the method of the present invention. In an interdigital cantilever array, interleaved fingers are built onto a cantilever in the form of a grid. The cantilever deflects one pair of fingers while the other remains stationery.

The method of the present invention is not limited to the particular embodiments disclosed herein and can be employed to detect any chemical interaction between naturally occurring bio-polymers which are non-identical binding partners with accuracy and at a low cost.

We claim:

1. A method of detecting an interaction between first biological analyte molecules and second biological analyte molecules, which first and second biological analyte molecules are non-identical binding partners, comprising:

preparing at least one cantilever by attaching the first biological analyte molecules to a surface of the at least one cantilever;

introducing the second biological analyte molecules to the surface of the at least one cantilever; and detecting a change in position of the at least one cantilever.

2. The method of detecting an interaction recited in claim 1, wherein the first biological analyte molecules or the second biological analyte molecules are monomers.

3. The method of detecting an interaction recited in claim 1, wherein the first biological analyte molecules or the second biological analyte molecules are polymers.

4. The method of detecting an interaction recited in claim 1, wherein the first biological analyte molecules or the second biological analyte molecules are oligonucleotides.

5. The method of detecting an interaction recited in claim 1, wherein the first biological analyte molecules or the second biological analyte molecules are DNA.

6. The method of detecting an interaction recited in claim 1, wherein the first biological analyte molecules or the second biological analyte molecules are nucleic acid arrays.

7. The method of detecting an interaction recited in claim 1, wherein the first biological analyte molecules or second biological analyte molecules are protein arrays.

8. The method of detecting an interaction recited in claim 1, wherein the first biological analyte molecules or the second biological analyte molecules are polypeptide arrays.

9. The method of detecting an interaction recited in claim 1, wherein the first biological analyte molecules or the second biological analyte molecules are carbohydrate arrays.

10. The method of detecting an interaction recited in claim 1, wherein the change in position of the at least one cantilever is caused by stress induced on the at least one cantilever by an interaction between the first biological analyte molecules and the second biological analyte molecules.

11. The method of detecting an interaction recited in claim 1, wherein the change in position of the at least one cantilever is caused by a thermal change induced on the at least one cantilever by an interaction between the first biological analyte molecules and the second biological analyte molecules.

12. The method of detecting an interaction recited in claim 1, wherein the change in position of the at least one cantilever is detected by measuring a frequency shift in the resonant frequency of the at least one cantilever.

13. The method of detecting an interaction recited in claim 1, wherein the change in position of the at least one cantilever is detected by measuring light reflected from the at least one cantilever.

14. The method of detecting an interaction recited in claim 13, wherein the light reflected from the at least one cantilever is measured using a split photodiode.

15. The method of detecting an interaction recited in claim 13, wherein the light reflected from the at least one cantilever is measured using a linear array of photodetectors.

16. The method of detecting an interaction recited in claim 13, wherein the light reflected from the at least one cantilever is measured using piezo resistance elements.

17. The method of detecting an interaction recited in claim 1, wherein the detected change in position of the at least one cantilever is compared with a detected change in position of at least a second cantilever to which the first biological analyte molecules have not been attached.

18. The method of detecting an interaction recited in claim 1, wherein
the first analyte molecules are attached to a plurality of first cantilevers, the first cantilevers being interleaved with second cantilevers to which the first analyte molecules are not attached such that the first and second cantilevers form a grating,
and further comprising:
reflecting light off of the grating; and
detecting a change in position of the first cantilevers by measuring an intensity of diffracted modes of light reflected off of the grating.

19. The method of detecting an interaction recited in claim 1, wherein the surface of the at least one cantilever is silicon dioxide.

20. The method of detecting an interaction recited in claim 1, wherein the change in position of the at least one cantilever detects affinity binding between the first analyte molecules and the second analyte molecules.

21. The method of detecting an interaction recited in claim 20, wherein the change in position of the at least one cantilever detects hydrogen bonding between the first analyte molecules and the second analyte molecules.

22. A The method of detecting an interaction recited in claim 1, wherein the change in position of the at least one cantilever detects electrostatic attraction between the first analyte molecules and the second analyte molecules.

23. The method of detecting an interaction recited in claim 1, wherein the change in position of the at least one cantilever detects hydrophobic effects between the first analyte molecules and the second analyte molecules.

24. The method of detecting an interaction recited in claim 1, wherein the change in position of the at least one cantilever detects dipole interactions between the first analyte molecules and the second analyte molecules.

* * * * *